US00PP22182P2

(12) United States Plant Patent
Hanes

(10) Patent No.: US PP22,182 P2
(45) Date of Patent: Oct. 4, 2011

(54) ***PETUNIA* PLANT NAMED 'PIC WHIT'**

(50) Latin Name: *Petunia hybrida*
Varietal Denomination: Pic Whit

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 158 days.

(21) Appl. No.: 12/653,685

(22) Filed: Dec. 17, 2009

(51) Int. Cl.
*A01H 5/00* (2006.01)

(52) U.S. Cl. ..... Plt./356.15

(58) Field of Classification Search ..... Plt./356.15
See application file for complete search history.

(56) References Cited

U.S. PATENT DOCUMENTS

PP11,595 P * 10/2000 Westhoff ..... Plt./356.15
PP12,818 P2 * 7/2002 Brown ..... Plt./356.15
PP19,586 P2 * 12/2008 van Kleinwee ..... Plt./356.15

OTHER PUBLICATIONS

UPOV ROM GTITM Computer Database, GTI Jouve Retrieval Software 2011/01 "CA" Citation for 'Pic Whit'.*
UPOV ROM GTITM Computer Database, GTI Jouve Retrieval Software 2011/01 "QZ" Citation for 'Pic Whit'.*

* cited by examiner

*Primary Examiner* — Wendy C Haas
(74) *Attorney, Agent, or Firm* — S. Matthew Edwards

(57) ABSTRACT

A new *Petunia* plant named 'Pic Whit,' particularly distinguished by the small white flowers, early blooming, very good floriferousness, and a strong semi-trailing plant habit.

1 Drawing Sheet

Latin name of the genus and species of the plant claimed: *Petunia hybrida.*

Varietal denomination: 'Pic Whit'.

BACKGROUND OF THE NEW PLANT

The present invention comprises a new *Petunia,* botanically known as *Petunia hybrida,* and hereinafter referred to by the variety name 'Pic Whit.'

'Pic Whit' is a product of a planned breeding program. The new cultivar has small white flowers, early blooming, very good floriferousness and a strong semi-trailing plant habit.

'Pic Whit' originated from a hybridization made in August 2004 in a controlled breeding environment in Gilroy, Calif. The resultant seed was sown in February 2005. The female parent was the proprietary plant designated '1695-3', unpatented, with pink small flowers and larger foliage.

The male parent of 'Pic Whit' was identified as '1691-1', a unpatented, proprietary plant with light pinkish flowers. '1691-1' has less vigor and little larger flowers than 'Pic Whit.'

'Pic Whit' was selected as one flowering plant within the progeny of the stated cross in May, 2005 in a controlled environment in Gilroy, Calif.

The first act of asexual reproduction of 'Pic Whit' was accomplished when vegetative cuttings were propagated from the initial selection in May 2005, in a controlled environment in Gilroy, Calif.

BRIEF SUMMARY OF INVENTION

Horticultural examination of plants grown from cuttings of the plant initiated in May 2005, and continuing thereafter, has demonstrated that the combination of characteristics as herein disclosed for 'Pic Whit' are firmly fixed and are retained through successive generations of asexual reproduction.

'Pic Whit' has not been observed under all possible environmental conditions. The phenotype may vary significantly with variations in environment such as temperature, light intensity and day length.

A Plant Breeder's Right for this cultivar was applied for in Canada on Jan. 30, 2009. 'Pic Whit' has not been made publicly available more than one year prior to the filing of this application.

The following traits have been repeatedly observed and are determined to be basic characteristics of the new variety. The combination of these characteristics distinguishes this *Petunia* as a new and distinct variety

BRIEF DESCRIPTION OF THE PHOTOGRAPHS

The accompanying photographic drawing shows typical flower and foliage characteristics of 'Pic Whit' with colors being as true as possible with an illustration of this type. The photographic drawing shows a flowering potted plant of the new variety, and a close-up of the flowers.

DETAILED BOTANICAL DESCRIPTION

The plant descriptions and measurements were taken in Gilroy, Calif. in July 2009, from plants growing outside in 10 inch basket trials, 3 plants per basket. These plants were approximately 14-16 weeks of age. The aforementioned photographs were taken in Gilroy, Calif. in early April 2009 in a fiberglass covered greenhouse. These plants were about 8-10 weeks old.

Color references are made to The Royal Horticultural Society Colour Chart (R.H.S.) 2001.

TABLE 1

DIFFERENCES BETWEEN THE NEW VARIETY 'PIC WHIT' AND A SIMILAR VARIETY

| | 'Pic Whit' | 'MP 21' (U.S. Plant Pat. No. 12,818) |
|---|---|---|
| Flower quantity: | More | Fewer |
| Peduncle length: | Shorter | Longer |
| Sepal length: | Shorter | Longer |

Plant:

*Form, growth and habit.*—Semi-compact to outwardly spreading and cascading; good vigorous habit, well branched, small foliage and early and continuous flowering.

*Plant height.*—14-17 cm.

*Plant height* (*inflorescence included*).—15-21 cm.

*Plant width.*—44-49 cm.

*Garden performance and tolerance to weather.*—Very good.

*Crop time to flowering.*—About 7-8 weeks.

Roots:

*Number of days to initiate roots.*—18-23 days at about 22 degrees C.

*Number of days to produce a rooted cutting.*—At 22 degrees C.

*Type.*—Fine, fibrous, free branching.

*Color.*—RHS N155B but whiter.

Foliage:

*Arrangement.*—Alternate, upper leaves sub-alternate.

*Immature, leaf color, upper surface.*—Closest to RHS 147B but greener.

*Immature, leaf color, lower surface.*—RHS 14B but lighter.

*Mature, leaf color, upper surface.*—Closest to RHS 147B but greener.

*Mature, leaf color, lower surface.*—RHS 146B but lighter.

*Length.*—2.9-3.3 cm.

*Width.*—1.7-2.0 cm.

*Shape.*—Ovate.

*Base.*—Attenuate.

*Apex shape.*—Acute.

*Margin.*—Entire.

*Texture, upper surface.*—Glandular hairs.

*Texture, lower surface.*—Glandular hairs.

*Color of veins, upper surface.*—RHS 146D.

*Color of veins, lower surface.*—RHS 146D.

*Petiole color.*—RHS 146D.

*Length.*—0.3 cm.

*Diameter.*—0.2 cm.

*Texture.*—Glandular hairs.

Stem:

*Color of stem.*—Closest to RHS 146B.

*Length of stem.*—25-40 cm.

*Diameter.*—0.2-0.3 cm.

*Length of internodes.*—0.5-1.5 cm.

*Texture.*—Glandular hairs.

*Color of peduncles.*—Closest to RHS 146B.

*Length of peduncles.*—1.8-2.1 cm.

*Diameter of peduncles.*—0.1 cm.

*Texture.*—Glandular hairs.

Inflorescence:

*Type.*—Flowers appear solitary in upper leaf axis. Floret type, Funnel-shaped; 5 lobed petals; fused at the base; calyx, 5 deeply lobed sepals.

*Blooming habit.*—Continuous throughout the growing season; good floriferousness.

*Quantity of inflorescences per plant.*—Approximately 100.

*Lastingness of individual blooms on the plant.*—4-8 days.

*Fragrance.*—Slightly sweet and spicy.

Bud: (Just starting to open/show color)

*Color.*—RHS 1C.

*Length.*—2.2-2.5 cm.

*Width.*—0.4-0.5 cm.

*Shape.*—Oblong.

Immature inflorescence:

*Diameter.*—2.9-3.1 cm.

*Color, upper surface.*—RHS N155B but whiter with RHS N144A mid-veins.

*Color, lower surface.*—RHS N 155B but whiter with RHS N144A mid-veins.

Mature inforescence:

*Floret horizontal diameter.*—3.3-3.6 cm.

*Vertical depth.*—2.2-2.5 cm.

*Petal color, upper surface.*—RHS N155B but whiter with RHS N144A mid-veins.

*Petal color, lower surface.*—RHS N155B but whiter with RHS N144A mid-veins.

*Petal apex shape.*—Slightly retuse.

*Petal base shape.*—Fused.

*Petal margin.*—Entire.

*Waviness of petals.*—Very little.

*Petal lobation.*—Moderate.

*Petal texture.*—Papillose.

*Corolla tube color inside.*—RHS N 155B but whiter, slightly overlaid with RHS 3C, with RHS 1A mid-veins.

*Corolla tube color outside.*—RHS N155B but whiter, slightly overlaid with a light RHS 1B; with RHS N144 mid-veins.

*Corolla tube length.*—1.8-1.9 cm.

*Corolla texture, inside.*—Papillose.

*Corolla texture, outside.*—Glandular hairs.

Sepals:

*Color, upper surface.*—RHS 146A.

*Color, lower surface.*—RHS 146B.

*Length.*—0.8-0.9 cm.

*Width.*—0.15-0.2 cm.

*Shape.*—Oblong.

*Apex shape.*—Obtuse.

*Margins.*—Entire.

*Base.*—Fused.

*Texture, upper surface.*—Glandular hairs.

*Texture, lower surface.*—Glandular hairs.

Reproductive organs:

*Pistil.*—1.

*Length.*—1.6-1.7 cm.

*Style color.*—RHS 144C.

*Style length.*—1.4-1.6 cm.

*Stigma color.*—RHS 144A but a little lighter.

*Ovary color.*—Not observed.

*Stamens.*—5.

*Color of filaments.*—RHS 145C.

*Length filaments.*—1.0-1.5 cm.

*Anther color.*—About 155C.
*Anther length.*—About 0.2 cm.
*Anther shape.*—Reniform.
*Color of pollen.*—RHS 2D.
*Pollen amount.*—Moderate.
*Fertility/seed set.*—Has not been observed on this hybrid.

Disease/pest resistance: Resistance or susceptibility has not been observed on this hybrid.

What is claimed is:

1. A new and distinct variety of *Petunia* plant named 'Pic Whit,' substantially as illustrated and described herein.

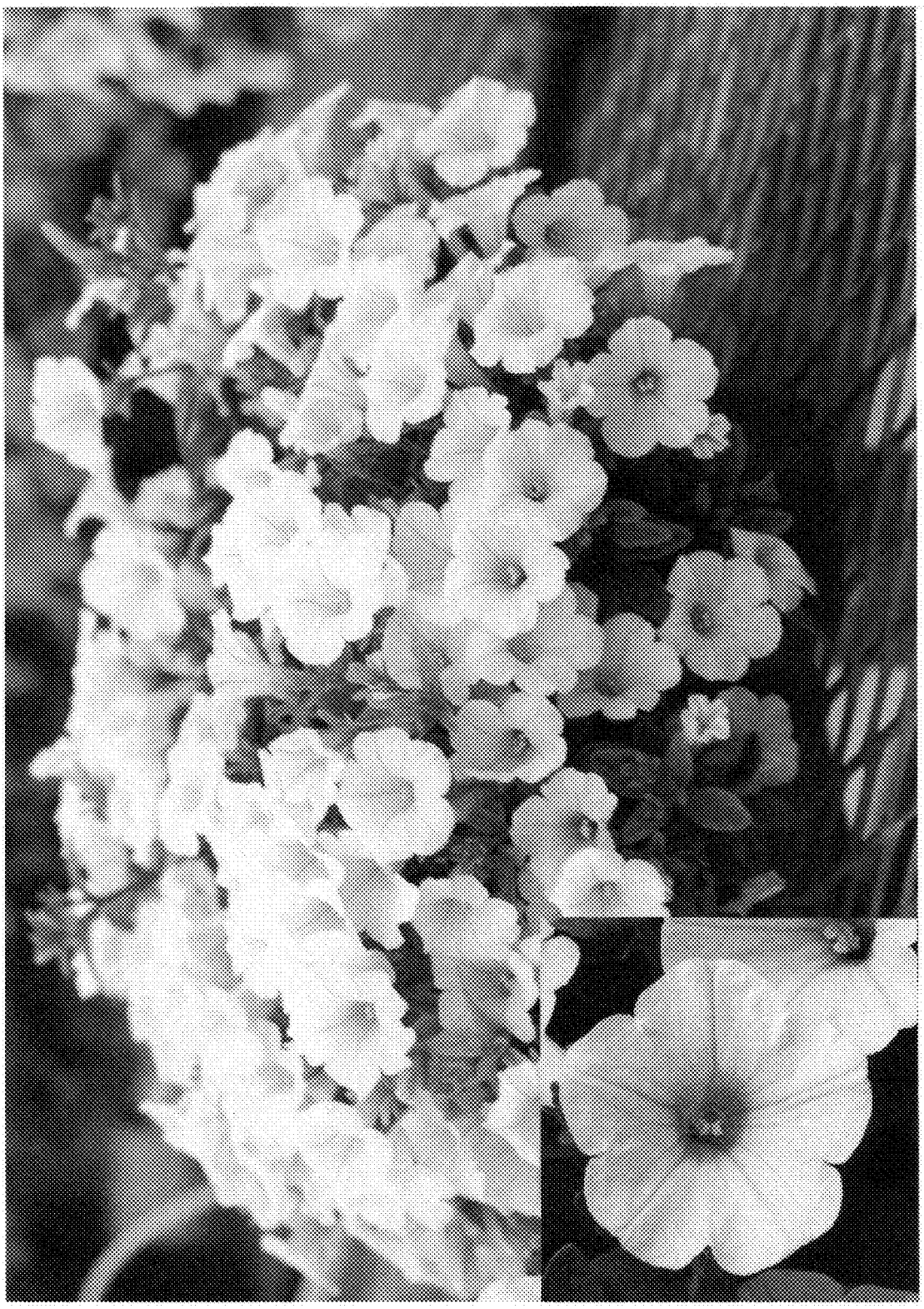

* * * * *